US008358340B2

(12) United States Patent
Yoshikawa et al.

(10) Patent No.: US 8,358,340 B2
(45) Date of Patent: Jan. 22, 2013

(54) PATTERN INSPECTION DEVICE AND METHOD OF INSPECTING PATTERN

(75) Inventors: Ryoji Yoshikawa, Kanagawa (JP);
Tomohide Watanabe, Kanagawa (JP);
Hiromu Inoue, Kanagawa (JP);
Hiroyuki Ikeda, Kanagawa (JP);
Hiroyuki Tanizaki, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 903 days.

(21) Appl. No.: 12/477,666

(22) Filed: Jun. 3, 2009

(65) Prior Publication Data
US 2009/0303323 A1 Dec. 10, 2009

(30) Foreign Application Priority Data

Jun. 4, 2008 (JP) .................. 2008-146871

(51) Int. Cl.
*H04N 7/18* (2006.01)
*H04N 9/47* (2006.01)
(52) U.S. Cl. .......................................... 348/92
(58) Field of Classification Search ............ 348/92
See application file for complete search history.

(56) References Cited

U.S. PATENT DOCUMENTS

| 6,529,621 | B1* | 3/2003 | Glasser et al. ........... 382/144 |
| 6,656,648 | B2 | 12/2003 | Inoue |
| 6,846,597 | B2* | 1/2005 | Narukawa et al. ......... 430/5 |
| 7,014,955 | B2* | 3/2006 | Chang et al. ........... 430/5 |
| 7,697,746 | B2* | 4/2010 | Kawaguchi ......... 382/149 |
| 2001/0055416 | A1* | 12/2001 | Yamashita ........... 382/149 |
| 2009/0175530 | A1* | 7/2009 | Sjostrom et al. ......... 382/152 |

FOREIGN PATENT DOCUMENTS

| JP | 7-128248 | 5/1995 |
| JP | 2001-281160 | 10/2001 |
| JP | 2004-191957 | 7/2004 |
| JP | 2008-64553 | 3/2008 |

OTHER PUBLICATIONS

Notification of Reason for Rejection issued by the Japanese Patent Office on May 8, 2012, for Japanese Patent Application No. 2008-146871, and English-language translation thereof.

* cited by examiner

*Primary Examiner* — Kristie Shingles
(74) *Attorney, Agent, or Firm* — Finnegan, Henderson, Farabow, Garrett & Dunner, L.L.P.

(57) ABSTRACT

A pattern inspection device according to the embodiment, includes: an image picking-up portion for picking-up an image of a pattern formation member in which a plurality of opening patterns are formed so as to obtain a picked-up image of the pattern formation member; a reference image obtaining portion for obtaining a reference image used for comparing with the picked-up image; and a pattern defect detecting portion for matching the center locations of the opening pattern images respectively between the picked-up image and the reference image, forming difference images of the opening pattern images between the picked-up image and the reference image per the opening pattern and detecting the defect of the opening pattern base on the difference images.

11 Claims, 10 Drawing Sheets

100 MASK PATTERN IMAGE

101 CONTACT PATTERN IMAGE
102 DUMMY PATTERN IMAGE

FIG.4

|     |     |     |     |     |     |     |     |     |     |     |
|-----|-----|-----|-----|-----|-----|-----|-----|-----|-----|-----|
| 244 | 244 | 244 | 242 | 241 | 241 | 241 | 241 | 243 | 244 | 244 |
| 244 | 243 | 238 | 231 | 224 | 221 | 221 | 224 | 231 | 238 | 243 | 244 |
| 243 | 235 | 213 | 183 | 160 | 152 | 154 | 164 | 189 | 218 | 238 | 243 |
| 239 | 216 | 161 | 96  | 64  | 55  | 56  | 69  | 108 | 175 | 226 | 242 |
| 235 | 196 | 109 | 38  | 33  | 40  | 38  | 31  | 47  | 129 | 211 | 239 |
| 232 | 183 | 84  | 31  | 56  | 76  | 73  | 49  | 33  | 106 | 202 | 238 |
| 231 | 180 | 80  | 32  | 66  | 89  | 86  | 57  | 33  | 101 | 200 | 237 |
| 232 | 184 | 85  | 31  | 55  | 75  | 73  | 48  | 34  | 106 | 203 | 237 |
| 234 | 197 | 111 | 37  | 32  | 41  | 39  | 31  | 47  | 132 | 212 | 239 |
| 238 | 216 | 159 | 90  | 56  | 47  | 49  | 62  | 104 | 174 | 225 | 241 |
| 242 | 234 | 210 | 176 | 150 | 141 | 142 | 155 | 183 | 216 | 236 | 242 |
| 243 | 241 | 236 | 228 | 221 | 217 | 218 | 221 | 229 | 237 | 242 | 243 |
| 244 | 243 | 242 | 242 | 241 | 240 | 240 | 241 | 242 | 243 | 243 | 244 |

110b — 101 CONTACT PATTERN IMAGE

110c

FIG.7A (N=3)  101 CONTACT PATTERN IMAGE

| 244 | 244 | 244 | 242 | 241 | 241 | 241 | 241 | 243 | 244 | 244 | 244 |
|-----|-----|-----|-----|-----|-----|-----|-----|-----|-----|-----|-----|
| 244 | 243 | 238 | 231 | 224 | 221 | 221 | 224 | 231 | 238 | 243 | 244 |
| 243 | 235 | 213 | 183 | 160 | 152 | 154 | 164 | 189 | 218 | 238 | 243 |
| 239 | 216 | 161 | 96  | 64  | 55  | 56  | 69  | 108 | 175 | 226 | 242 |
| 235 | 196 | 109 | 38  | 33  | 40  | 38  | 31  | 47  | 129 | 211 | 239 |
| 232 | 183 | 84  | 31  | 56  | 76  | 73  | 49  | 33  | 106 | 202 | 238 |
| 231 | 180 | 80  | 32  | 66  | 89  | 86  | 57  | 33  | 101 | 200 | 237 |
| 232 | 184 | 85  | 31  | 55  | 75  | 73  | 48  | 34  | 109 | 203 | 237 |
| 234 | 197 | 111 | 37  | 32  | 41  | 39  | 31  | 47  | 132 | 212 | 239 |
| 238 | 216 | 159 | 90  | 56  | 47  | 49  | 62  | 104 | 174 | 225 | 241 |
| 242 | 234 | 210 | 176 | 150 | 141 | 142 | 155 | 183 | 216 | 236 | 242 |
| 243 | 241 | 236 | 228 | 221 | 217 | 218 | 221 | 229 | 237 | 242 | 243 |
| 244 | 243 | 242 | 242 | 241 | 240 | 240 | 241 | 242 | 243 | 243 | 244 |

114 SUMMATION CALCULATION REGION

$$\text{COEFFICIENT} = \begin{pmatrix} 1 & 2 & 1 \\ 2 & 4 & 2 \\ 1 & 2 & 1 \end{pmatrix}$$

| 244 | 244 | 244 | 242 | 241 | 241 | 241 | 241 | 243 | 244 | 244 | 244 |
|---|---|---|---|---|---|---|---|---|---|---|---|
| 244 | 243 | 238 | 231 | 224 | 221 | 221 | 224 | 231 | 238 | 243 | 244 |
| 243 | 235 | 213 | 183 | 160 | 152 | 154 | 164 | 189 | 218 | 238 | 243 |
| 239 | 216 | 161 | 96 | 64 | 55 | 56 | 69 | 109 | 175 | 226 | 242 |
| 235 | 196 | 109 | 38 | 33 | 40 | 38 | 31 | 47 | 129 | 211 | 239 |
| 232 | 183 | 84 | 31 | 56 | 76 | 73 | 49 | 33 | 106 | 202 | 238 |
| 231 | 180 | 80 | 32 | 66 | 89 | 86 | 57 | 33 | 101 | 200 | 237 |
| 232 | 184 | 85 | 31 | 55 | 75 | 73 | 48 | 34 | 108 | 203 | 237 |
| 234 | 197 | 111 | 37 | 32 | 41 | 39 | 31 | 47 | 132 | 212 | 239 |
| 238 | 216 | 159 | 90 | 56 | 47 | 49 | 62 | 104 | 174 | 225 | 241 |
| 242 | 234 | 210 | 176 | 150 | 141 | 142 | 155 | 183 | 216 | 236 | 242 |
| 243 | 241 | 236 | 228 | 221 | 217 | 218 | 221 | 229 | 237 | 242 | 243 |
| 244 | 243 | 242 | 242 | 241 | 240 | 240 | 241 | 242 | 243 | 243 | 244 |

101

114

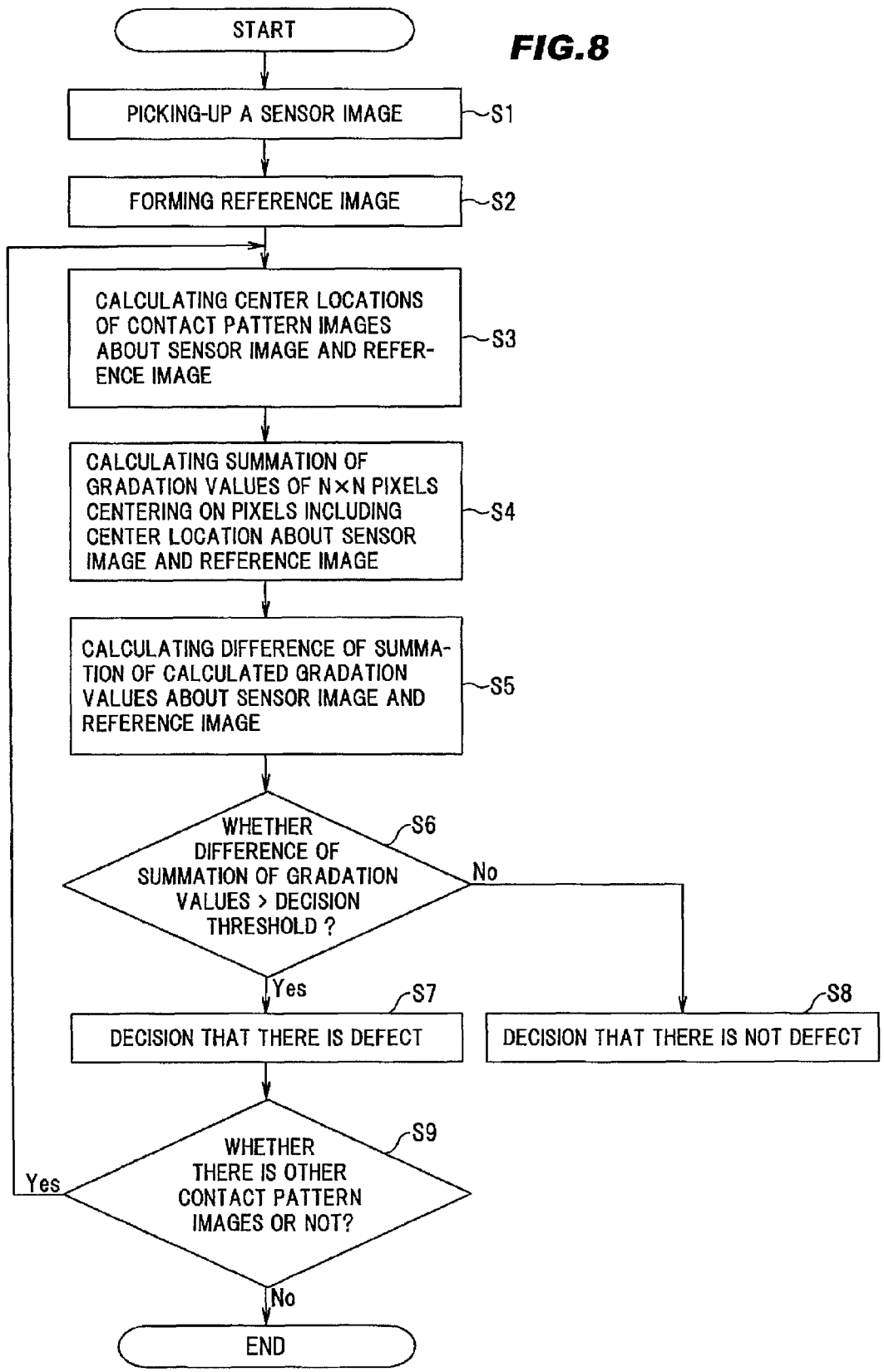

PATTERN INSPECTION DEVICE AND METHOD OF INSPECTING PATTERN

CROSS-REFERENCE TO RELATED APPLICATIONS

This application is based upon and claims the benefit of priority from prior Japanese Patent Application No. 2008-146871, filed on Jun. 4, 2008, the entire contents of which are incorporated herein by reference.

BACKGROUND

Conventionally, a pattern inspection device is known, that inspects whether there is defect or not by comparing a sensor image obtained by taking an image of a mask with a reference image to be a criterion. This method is, for example, disclosed in JP-A-2008-64553.

The pattern inspection device includes an image sensor for taking an image of a mask on which a plurality of contact patterns are formed so as to obtain an sensor image, a reference image forming portion for deploying design data of the mask so as to form the reference image, a difference image preparing portion for preparing difference images between the sensor image and the referential image in the whole of the mask, and a deciding portion for deciding whether there is defect or not based on a gradation value in a part of a region corresponding to the contact pattern of the difference image.

According to the conventional pattern inspection device, there is a problem that if there is a matching residual of alignment in the contact pattern, it can not be differentiated whether the difference of the detected difference image has been caused by the matching residuals or by the shape defect of the mask, so that detection sensitivity can not be enhanced.

BRIEF SUMMARY

A pattern inspection device according to the embodiment, includes: an image picking-up portion for picking-up an image of a pattern formation member in which a plurality of opening patterns are formed so as to obtain a picked-up image of the pattern formation member; a reference image obtaining portion for obtaining a reference image used for comparing with the picked-up image; and a pattern defect detecting portion for matching the center locations of the opening pattern images respectively between the picked-up image and the reference image, forming difference images of the opening pattern images between the picked-up image and the reference image per the opening pattern and detecting the defect of the opening pattern base on the difference images.

A method of inspecting a pattern according to another embodiment, includes: obtaining a picked-up image by picking-up an image of a pattern formation member in which a plurality of opening patterns are formed; obtaining a reference image used for comparing with the picked-up image; matching the center locations of the opening pattern images respectively between the picked-up image and the reference image, and forming difference images of the opening pattern images between the picked-up image and the reference image per the opening pattern; and detecting the defect of the opening pattern based on the difference images.

BRIEF DESCRIPTION OF THE DRAWING

FIG. 4 is an explanatory view schematically showing one example of a template for contact pattern decision;

FIGS. 7A to 7C are explanatory views schematically showing respective calculation examples of summation of gradation values in case of N=3, N=2 or N=1; and FIG. 8 is a flowchart schematically showing an operation of the pattern inspection device according to one embodiment.

DETAILED DESCRIPTION

Figure 1A:
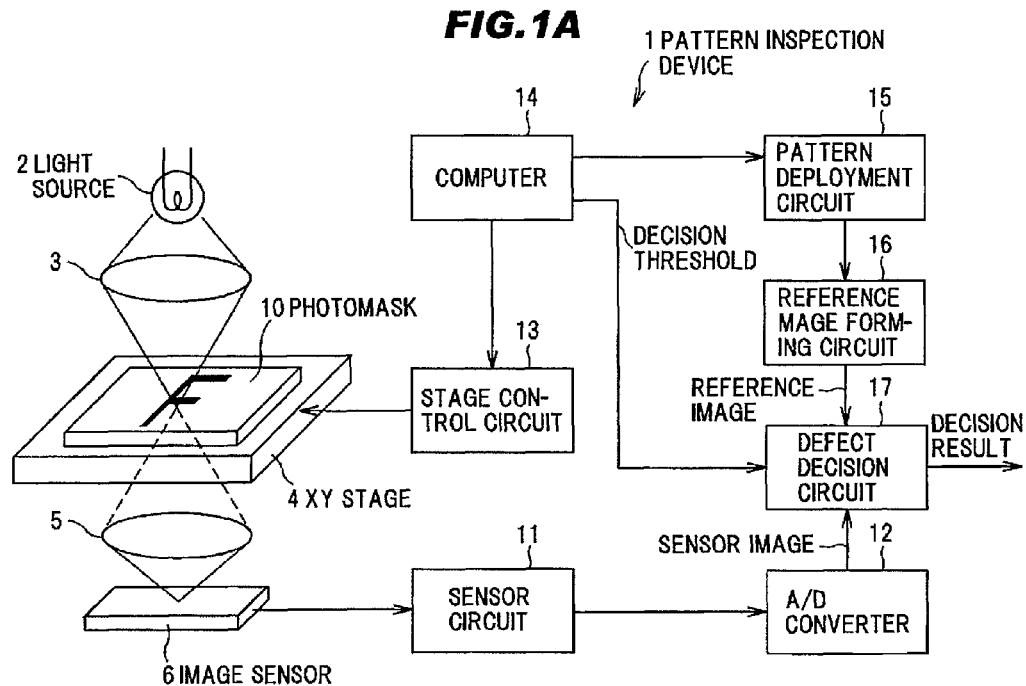
FIG. 1A is a block diagram schematically showing a configuration of a pattern inspection device according to one embodiment.
Figure 1B:
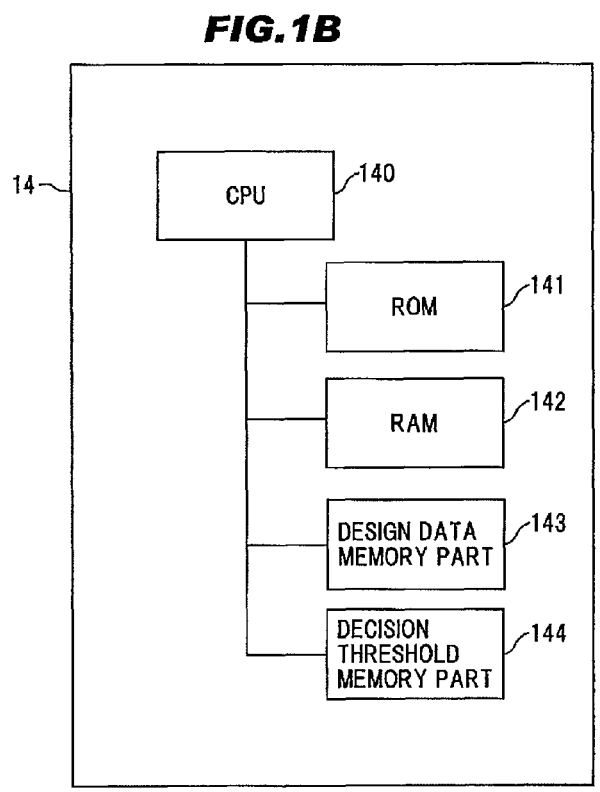
FIG. 1B is a block diagram schematically showing a configuration of a computer used for one embodiment.

FIG. 1A is a block diagram schematically showing a configuration of a pattern inspection device according to one embodiment, and FIG. 1B is a block diagram schematically showing a configuration of a computer used for one embodiment.

As shown in FIG. 1A, the pattern inspection device 1 includes, on the optical axis, a light source 2 such as a mercury lamp and an argon laser, a collecting lens 3, an XY stage 4 on which a photomask (pattern formation member) 10 as an inspection object is disposed, an objective lens 5, and an image sensor 6, and further, includes a sensor circuit 11, an A/D converter 12, a stage control circuit 13, a computer 14, a pattern deployment circuit 15, a reference image occurrence circuit (reference image obtaining portion) 16 and a defect decision circuit (pattern defect detecting portion) 17.

The light source 2, the collecting lens 3, the objective lens 5 and the image sensor 6 constitute an image picking-up portion which picks-up an image of a pattern of the photomask 10 so as to obtain a picked-up image.

In the photomask 10, mask patterns including a plurality of contact patterns (opening patterns) are formed. The contact pattern is used for forming contact holes in a contact layer in a process of manufacturing a wafer of a semiconductor memory and the like as one example of a semiconductor device. The contact pattern is an opening formed in a square shape (for example, 400 nm×400 nm), however, can be formed in other shapes such as a rectangle shape. Defects may occur in an edge portion or a central portion of the contact pattern, and the device 1 is used for inspecting whether there is the defect or not.

Further, the opening pattern is not limited to the contact pattern, the other patterns can be also used. And, as the photomask 10, a phase shift mask etc. having a semitransparent film can be also used.

The XY stage 4 is configured to allow the photomask 10 to move in the horizontal two axis directions (XY directions).

The stage control circuit 13 makes the XY stage 4 move in the X direction and the Y direction under the control of the computer 14 so that the XY stage 4 is able to scan the whole of the photomask 10.

As the image sensor 6, for example, a CCD sensor where CCDs (Charge Coupled Devices) are disposed in one dimensional or two dimensional alignment can be used. Even if the light-receiving area of the image sensor 6 is small, by making the photomask 10 move in the X direction and the Y direction relatively to the image sensor 6, the pattern image of the whole of photomask 10 can be picked-up. The pattern image of the photomask 10 is formed onto the image sensor 6 in a state of being magnified, for example, several hundred times according to the optical system such as the collecting lens 3 and the objective lens 5. Further, according to the characteristic of the photomask 10, instead of using the transmitted light, by using a reflected light or a mixed light of the transmitted light and the reflected light, the image can be also formed onto the image sensor 6.

The sensor circuit 11 outputs an optical image (sensor image) based on the pattern image of the whole of photomask 10, the pattern image being obtained from the image sensor 6 by scanning the whole of photomask 10. The pixel size of the sensor image is, for example, 100 nm×100 nm.

The pattern deployment circuit 15 deploys the design data of the mask pattern to multiple-valued gradation data per pixel having degradation ability almost equal to that of the image sensor 6. Further, if the sensor image is two-valued, the pattern deployment circuit 15 deploys to two-valued data.

The reference image forming circuit 16 applies filtering treatment and the like to the deployment data so as to form a reference image which corresponds to the optical characteristic and the change of form caused by an etching process etc. of the pattern formed on the photomask, in order to compare with the picked-up image obtained by picking-up an image of the photomask 10. The pixel size of the reference image is equal to that of the sensor image, that is 100 nm×100 nm. Further, a method of obtaining the reference image for comparing with the picked-up image is not limited to the method of converting the design data to the reference image, but for example, a method of reading out from a memory portion which stores the reference image according to the design data, and a method of inputting from an input portion can be also used.

The defect decision circuit 17 matches center locations of the images of the opening patterns (images of the contact patterns or the dummy patterns) respectively between the sensor image transmitted from the sensor circuit 11 in a state of being converted into digital information by the A/D converter 12 and the reference image transmitted from the reference image occurrence circuit 16, and forms difference images of the images of the opening patterns between the picked-up image and the reference image per the opening patterns, and decides whether there is the defect of the opening patterns or not based on the difference images.

As shown in FIG. 1B, the computer 14 includes a CPU 140 for controlling each part of the pattern inspection device 1, a ROM 141 for storing such a program as shown in a flowchart of FIG. 8 described below, a RAM 142 for provisionally the data, a design data memory part 143 for storing the design data of the mask pattern and a decision threshold memory part 144. The design data obtained after OPC (optical Proximity Correction) are used, but the design data obtained before the OPC can be also used. The program can be provided by recording media such as CD-ROM or can be provided via networks such as the internet.

The decision threshold memory part 144 stores a first decision threshold for the contact pattern (for example, 50) and a second decision threshold for the dummy pattern (for example, 100) according to the design data. Each of the first and second decision thresholds is such a value that obtained if minimum gradation value is defined as "0" and maximum gradation value is defined as "255". The first and second decision thresholds are outputted to a threshold selection circuit 176 described below of the defect decision circuit 17 by the CPU 140.

(Defect Decision Circuit)

Figure 2:
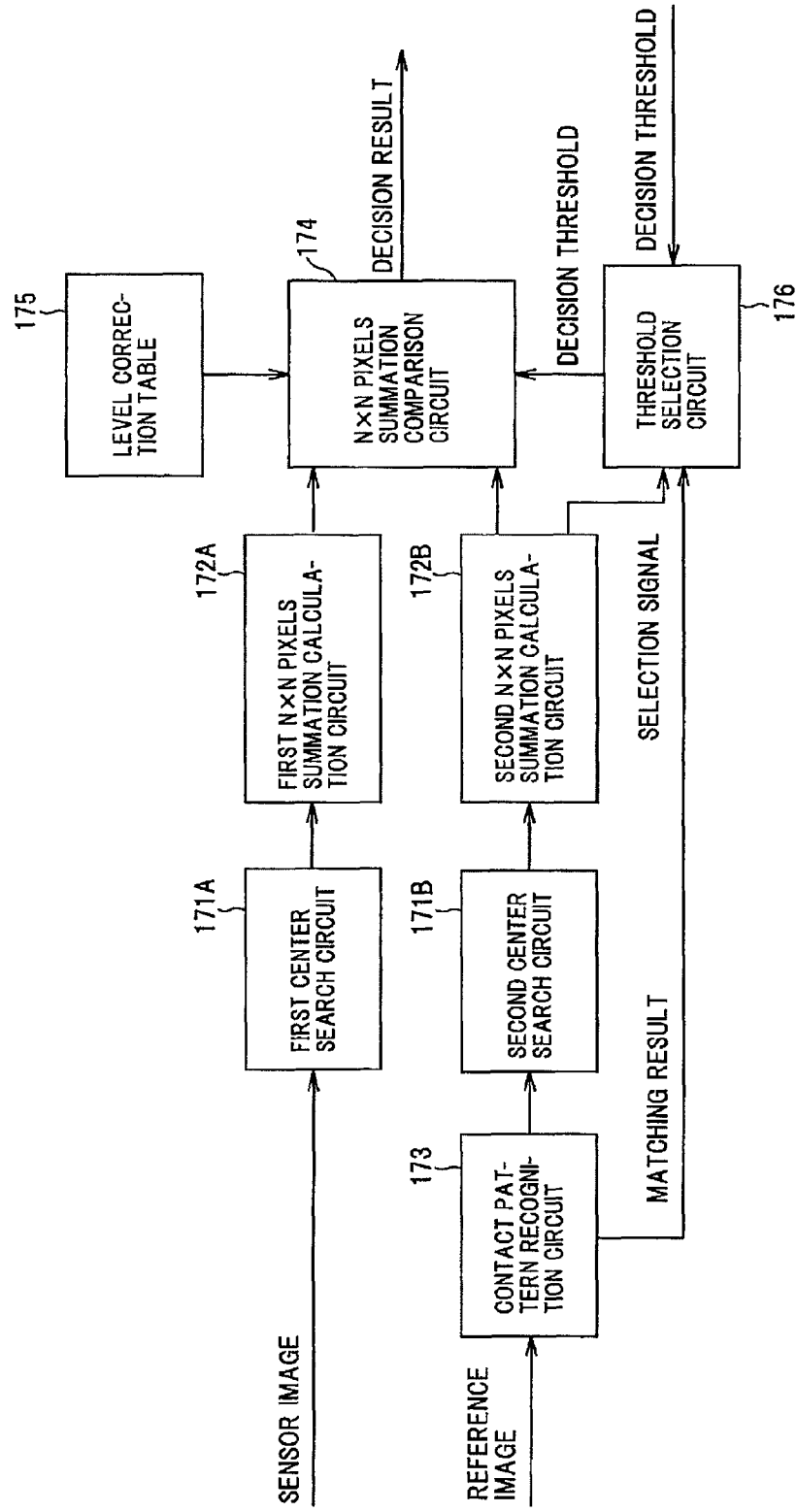
FIG. 2 is a block diagram schematically showing one example of a configuration of a defect decision circuit.
Figure 3:
FIG. 3 is an explanatory view schematically showing one example of a mask pattern image.
Figure 3:
Figure 3:
Figure 3:
Figure 3:
Figure 3:
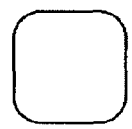
Figure 3:
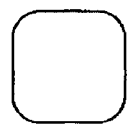
Figure 3:
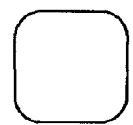
Figure 3:
Figure 3:
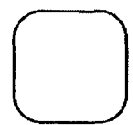
Figure 3:
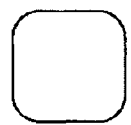
Figure 3:
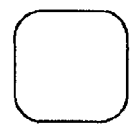
Figure 3:
Figure 3:
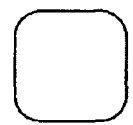
Figure 3:
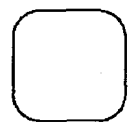
Figure 3:
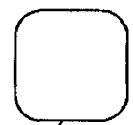
Figure 3:
Figure 5A:
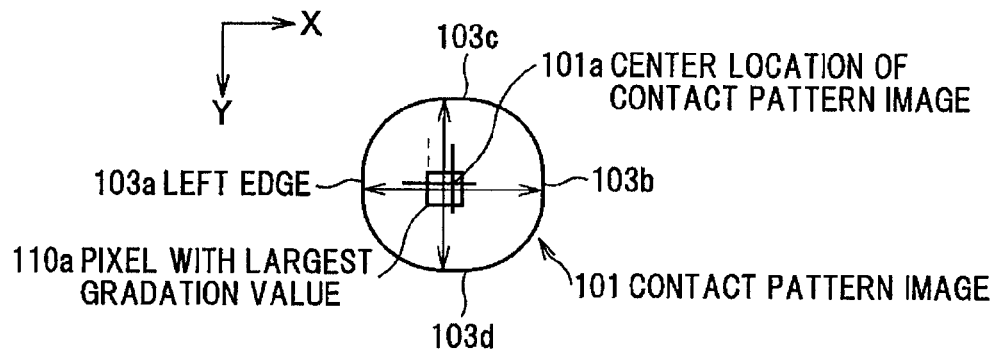
FIGS. 5A to 5D are explanatory views schematically showing a center search method by first and second center search circuits.
Figure 5B:
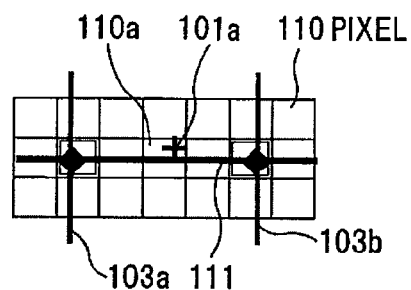
Figure 5C:
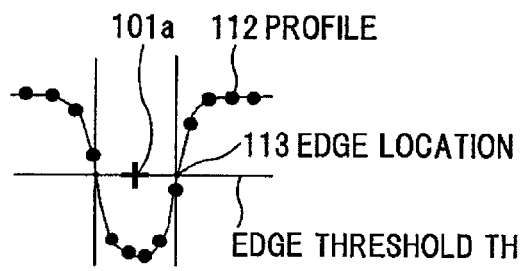
Figure 5D:
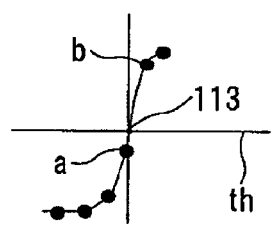
Figure 6:
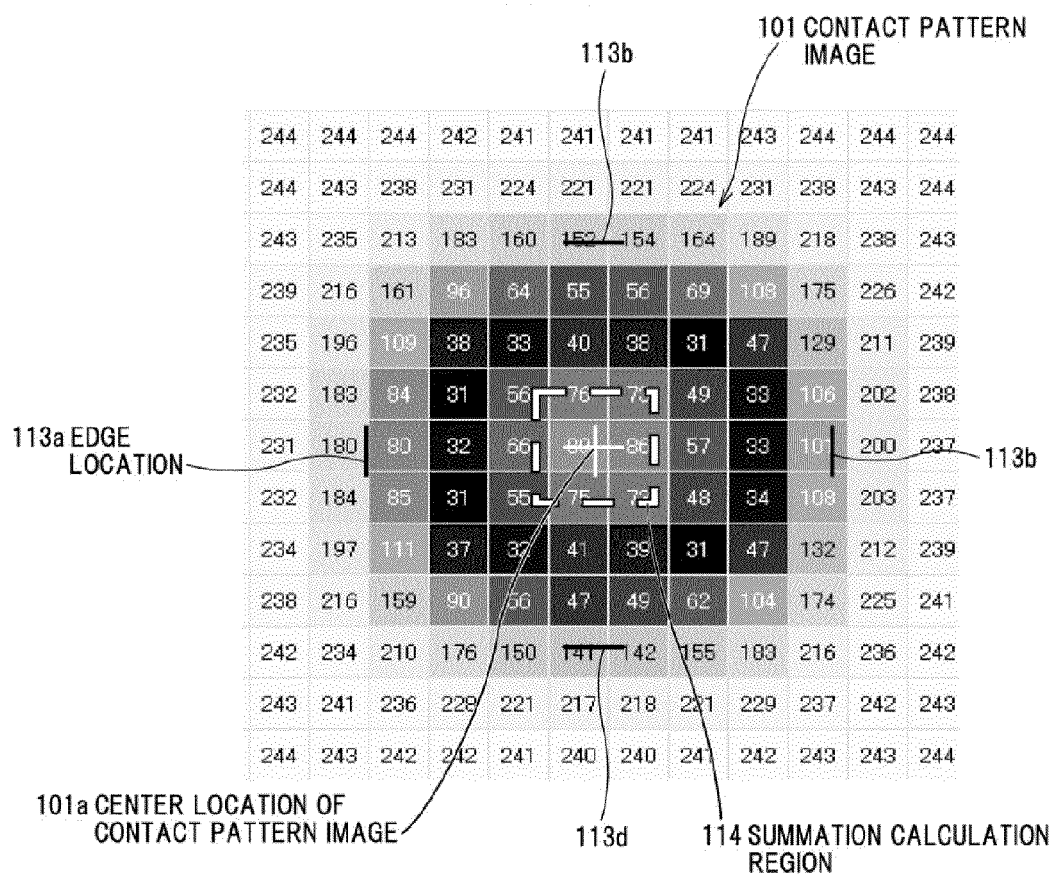
FIG. 6 is an explanatory view schematically showing one example of a gradation value adjacent to the contact pattern for explaining a method of calculating summation of gradation values by first and second N×N pixels summation calculation circuits.

FIG. 2 is a block diagram schematically showing one example of a configuration of the defect decision circuit 17, FIG. 3 is an explanatory view schematically showing one example of the mask pattern image, FIG. 4 is an explanatory view schematically showing one example of a template for contact pattern decision, FIGS. 5A to 5D are explanatory views schematically showing a center search method by first and second center search circuits, FIG. 6 is an explanatory view schematically showing one example of a gradation value adjacent to the contact pattern for explaining a method of calculating summation of gradation values by first and second N×N pixels summation calculation circuits and FIGS. 7A to 7C are explanatory views schematically showing respective calculation examples of summation of gradation values in case of N=3, N=2 or N=1.

As shown in FIG. 2, the defect decision circuit 17 includes two input lines of the sensor image and reference image, and the input line of the sensor image has a first center search circuit (detection part of center location) 171A and a first N×N pixels summation calculation circuit (summation calculation part) 172A, and the input line of the reference image has a contact pattern recognition circuit 173, a second center search circuit (detection part of center location) 171B and a second N×N pixels summation calculation circuit (summation calculation part) 172B. Further, the defect decision circuit 17 has a N×N pixels summation comparison circuit (summation comparison part) 174 connected to output sides of the first and second N×N pixels summation calculation circuits 172A, 172B, and has a level correction table 175 and a threshold selection circuit 176 connected to the N×N pixels summation comparison circuit 174.

(Mask Pattern Image)

The mask pattern includes a dummy pattern disposed adjacent to the region where the contact pattern exists in order to equalize an influence of the process proximity to the contact pattern. As shown in FIG. 3, the mask pattern image 100 on the sensor image and reference image includes dummy pattern images 102 disposed adjacent to the region where the contact pattern images 101 are disposed lengthwise and breadthwise at a predetermined interval. The dummy pattern image 102 has a opening size (for example, 200 nm) smaller than that (for example, 400 nm) of the contact pattern 101.

(Contact Pattern Recognition Circuit)

The contact pattern recognition circuit 173 recognizes the contact pattern by pattern-matching of the pattern image of the reference image and the template for the contact pattern decision.

With reference to FIG. 4, a method of recognizing the contact pattern will be explained. Values shown in FIG. 4 are gradation values of the reference image, and the case that quantity of light is maximum is defined as "255", and the case that quantity of light is minimum is defined as "0". The contact pattern recognition circuit 173 recognizes the objective pattern as the contact pattern image 101 if the gradation value of the pixel at a predetermined location satisfies a predetermined criterion, and outputs the result of the pattern-matching to the N×N pixels summation comparison circuit 174 via the threshold selection circuit.

Particularly, the contact pattern recognition circuit 173 recognizes the objective pattern as the contact pattern image 101, if the gradation values of pixels 110b which are enclosed with a heavy-line frame and disposed outside of the contact pattern image 101 to be a criterion are not less than a first criterion (for example, 180), and simultaneously, the gradation values of pixels 110c which are enclosed with a double line frame and disposed inside of the contact pattern image 101 to be a criterion are not more than a second criterion (for example, 80). In the case shown in FIG. 4, since the gradation values of pixels 110b enclosed with the heavy-line frame are in the range of 200 to 243 which are not less than the first criterion (180) and simultaneously, the gradation values of pixels 110c enclosed with the double line frame are in the range of 31 to 57 which are not more than the first criterion (80), the objective pattern is recognized as the contact pattern image 101.

(First and Second Center Search Circuits)

The first center search circuit 171A calculates the center location (x, y coordinates on the sensor image) of the contact pattern image 101 included in the sensor image. The second center search circuit 171B calculates the center location (x, y coordinates on the reference image) of the contact pattern image 101 included in the reference image. With reference to FIGS. 5A to 5D, a method of calculating the center location will be explained.

First, as shown in FIG. 5A, the location of the pixel 110a which has the largest gradation value in the contact pattern image 101 of the reference image is searched, and then a left edge 103a, a right edge 103b, an upper edge 103c and a lower edge 103d are searched in X, Y directions from the location respectively, and further, the center location 101a of the contact pattern image 101 is obtained from the locations of the edges 103a to 103d.

Particularly, as shown in FIG. 5B, a profile 112 of the gradation value on a line 111 from the pixel 110a having the largest gradation value in the X direction is prepared as shown in FIG. 5C. An edge location 113 at which the profile 112 crosses an edge threshold th is linearly-interpolated between the pixels, so that the edge location 113 is calculated with an accuracy of not more than the pixel size. In the profile 112 of FIG. 5C, if the edge location 113 of the right edge 103b is required to be obtained, as shown in FIG. 5D, the edge location 113 is calculated from the formula of $(b-th)/(b-a)$, when the gradation values adjacent to the edge location 113 are defined as a, b respectively. A location that is a distance of $(b-th)/(b-a)$ away from the location of the pixel having the gradation value a in the right direction is determined as the edge location 113. Similarly, the edge locations of the left edge 103a, the upper edge 103c and the lower edge 103d are obtained, and then the centers of pairs of the obtained edge locations is respectively obtained in the X direction or the Y direction, so that the center location 101a of the contact pattern image 101 is obtained.

(First and Second N×N Pixels Summation Calculation Circuit)

As shown in FIG. 6, the first and second N×N pixels summation calculation circuits 172A, 172B displace the center locations 101a of the respective contact pattern images 101 of the sensor image and reference image, the center locations 101a being obtained by the center search circuits 171A, 171B, to a center of summation calculation region 114 of N×N pixels, and then calculate the summation of the gradation values of the N×N pixels (N=1, 2, 3 . . . ). In FIG. 6, a white cross-shape mark shows the center location 101a of the contact pattern image 101 obtained by the center search circuits 171A, 171B, black horizontal and vertical lines show the edge locations 113a to 113d obtained by the center search circuits 171A, 171B, and a rectangular region enclosed with a white broken line shows the summation calculation region 114 at which the N×N pixels summation calculation circuits 172A, 172B calculate the summation of the gradation values.

In the case shown in FIG. 7A, if the summation of the gradation values of 3×3 pixels is calculated, the summation= (56+76+73+66+89+86+55+75+73)=649 is obtained. In the case shown in FIG. 7B, if the summation of the gradation values of 2×2 pixels is calculated, a coefficient shown in FIG. 7B corresponding to the pixel location is multiplied, a provisional summation is calculated, and a value obtained by dividing the provisional summation by 4 is determined as the summation. In the case shown in FIG. 7B, if the summation of the gradation values of 2×2 pixels is calculated, the summation=$(\frac{1}{4})\times\{(56\times1)+(76\times2)+(73\times1)+(66\times2)+(89\times4)+(86\times2)+(55\times1)+(75\times2)+(73\times1)\}$=305 is obtained. The summation of the gradation value of 1×1 pixel corresponds to the gradation value in the center, and in the case of FIG. 7c, the summation=89 is obtained.

Further, the N×N pixels summation calculation circuit 172B has also the following functions. That is, it calculates the summation of the gradation values about a region having a size almost the same as that of the opening size of the contact pattern image 101 of the reference image (7×7 pixels or 8×8 pixels), and if the summation is not less than the criterion value, decides it as the contact pattern image 101 so as to output a first selection signal to the threshold selection circuit 176, or if the summation is less than the criterion value, decides it as the dummy pattern image 102 so as to output a second selection signal to the threshold selection circuit 176.

(Level Correction Table)

The level correction table 175 is preliminarily prepared based on an experimental result, and it is used as a table that corrects brightness unevenness and the like due to the optical system in the sensor image.

(Threshold Selection Circuit)

The threshold selection circuit 176 selects a decision threshold from the first and second decision thresholds from the computer 104, based on the output from the second N×N pixels summation calculation circuit 172B. That is, the threshold selection circuit 176 selects the first decision threshold (for example, 50) for the contact pattern if the first selection signal is outputted from the N×N pixels summation calculation circuit 172B so as to output the first decision threshold to the N×N pixels summation comparison circuit 174, or it selects the second decision threshold (for example, 100) for the dummy pattern if the first selection signal is outputted from the N×N pixels summation calculation circuit 172B so as to output the second decision threshold to the N×N pixels summation comparison circuit 174.

Further, the location of N×N pixels of the region (summation calculation region) where the N×N pixels summation calculation circuits 172A, 172B calculate is not limited to the central portion of the contact pattern image, but a location on the edge portion or other locations can be also used. Furthermore, the size of the summation calculation region is not limited to N=1, 2, 3, but N=not less than 4 can be also used, and the size corresponding to the contact pattern image (for example, N=7 or 8) can be also used.

(N×N Pixels Summation Comparison Circuit)

The N×N pixels summation comparison circuit 174 calculates a difference between the summation of the gradation value obtained by the first N×N pixels summation calculation circuit 172A and the summation obtained after the correction that the summation of the gradation value obtained by the second N×N pixels summation calculation circuit 172B is corrected by using the level correction table 175. And, if the difference between the summations is larger than the first or second decision threshold provided from the threshold selection circuit 176, it decides as "there is defect" so as to output the decision result. The decision result includes information about whether the defect relates to the contact pattern or not based on the matching result from the contact pattern recognition circuit 173.

Further, the decision result of the defect to the dummy pattern can be configured not to be outputted from the N×N pixels summation comparison circuit 174 dependent on the matching result from the contact pattern recognition circuit 173 or the setting of the second decision threshold.

Operation of Embodiment

Next, an operation of the pattern inspection device 1 according to the embodiment will be explained with reference to a flowchart shown in FIG. 8.

Light generated at the light source 2 is collected on the photomask 10 according to the collecting lens 3. The light which is transmitted through the photomask 10 of the light collected on the photomask 10 is focused onto the light-receiving surface of the image sensor 6 according to the objective lens 5 (S1). The sensor circuit 11 outputs an optical image (sensor image) corresponding to the pattern image of the photomask 10 which is formed onto the light-receiving surface of the image sensor 6 to the defect decision circuit 17 via the A/D converter.

On the other hand, the CPU 140 of the computer 14 outputs the design data stored in the design data memory part 143 to the pattern deployment circuit 15, the pattern deployment circuit 15 deploys the design data to multiple-valued gradation data per pixel. The reference image forming circuit 16 applies filtering treatment and the like to the deployment data so as to form the reference image which corresponds to the optical characteristic and the change of form caused by an etching process etc., so as to output to the defect decision circuit (S2).

The contact pattern recognition circuit 173 of the defect decision circuit 17 recognizes the contact pattern 101 from the reference image by using the template for the contact pattern decision shown in FIG. 4, so as to output the matching result to the N×N pixels summation comparison circuit 174 via the threshold selection circuit 176.

As explained in FIGS. 5A to 5D, the second center search circuit 171B detects the contact pattern image 101 included in the reference image and calculates the center location 101a of the contact pattern image 101, so as to output the calculation result to the second N×N pixels summation calculation circuit 172B (S3).

As explained in FIGS. 5A to 5D, the first center search circuit 171A calculates the center location 101a of the contact pattern image 101 from the sensor image, so as to output the calculation result to the first N×N pixels summation calculation circuit 172A.

As explained in FIG. 6, the second N×N pixels summation calculation circuit 172B displaces the reference image so that the center locations 101a calculated by the second center search circuit 171B is located at the center of the pixel including the center location 101a, and then calculates the summation of the gradation values about the central region of N×N pixels (summation calculation region), so as to output the calculation result to the N×N pixels summation comparison circuit 174 (S4).

Further, the N×N pixels summation calculation circuit 172B calculates the summation of the gradation values about a region having a size almost the same as that of the opening size of the contact pattern image 101, and if the summation is not less than the criterion value, outputs the first selection signal to the threshold selection circuit 176, or if the summation is less than the criterion value outputs the second selection signal to the threshold selection circuit 176.

As explained in FIG. 6, the first N×N pixels summation calculation circuit 172A displaces the sensor image so that the center locations 101a calculated by the first center search circuit 171A is located at the center of the pixel including the center location 101a, and then calculates the summation of the gradation values about the central region of N×N pixels (summation calculation region), so as to output the calculation result to the N×N pixels summation comparison circuit 174.

The threshold selection circuit 176 selects the first decision threshold for the contact pattern if the first selection signal is outputted from the N×N pixels summation calculation circuit 172B so as to output the first decision threshold to the N×N pixels summation comparison circuit 174, or it selects the second decision threshold for the dummy pattern if the first selection signal is outputted from the N×N pixels summation calculation circuit 172B so as to output the second decision threshold to the N×N pixels summation comparison circuit 174.

The N×N pixels summation comparison circuit 174 calculates the difference between the summation of the gradation value obtained by the first N×N pixels summation calculation circuit 172A and the summation obtained after the correction that the summation of the gradation value obtained by the second N×N pixels summation calculation circuit 172B is corrected by using the level correction table 175 (S5).

The N×N pixels summation comparison circuit 174 decides as "there is defect" if the difference between the summations is larger than the first or second decision threshold provided from the threshold selection circuit 176 (S7), or decides as "there is not defect" if the difference between the summations is not larger than the first or second decision threshold provided from the threshold selection circuit 176 (S8). The decision result includes information about whether the defect relates to the contact pattern or not based on the matching result from the contact pattern recognition circuit 173.

If there is other contact pattern images (S9: Yes), the above-mentioned steps S3 to S8 are repeated.

Advantages of Embodiment

According to the embodiment, the following advantages are provided.
(1) Even if there is the matching residual of alignment in the contact pattern, the defect of the contact pattern can be detected with high accuracy.
(2) Defect detection accuracy can be enhanced by determining the location of the summation calculation region having a size smaller than that of the contact pattern according to the locations where the defect is likely to occur.
(3) Existence or nonexistence of the defect can be also decided without reducing the detection sensitivity for the mask in which the dummy patterns other than the contact patterns are formed.

Further, it should be noted that the present invention is not intended to be limited to the above-mentioned embodiment, and the various kinds of changes thereof can be implemented by those skilled in the art without departing from the gist of the invention.

Furthermore, a part or the whole of the circuits constituting the embodiment can be realized by software and the CPU.

What is claimed is:

1. A pattern inspection device, comprising:

an image picking-up portion for picking up an image of a pattern formation member in which a plurality of opening patterns are formed so as to obtain a picked-up image of the pattern formation member;

a reference image obtaining portion for obtaining a reference image used for comparing with the picked-up image;

a first center location detecting portion for detecting center locations of a plurality of opening pattern images included in the picked-up image;

a second center location detecting portion for detecting center locations of a plurality of opening pattern images included in the reference image;

a first summation calculation portion for calculating a summation of gradation values about regions predetermined by using the center locations of the picked-up image detected by the first center location detecting portion as a criterion;

a second summation calculation portion for calculating a summation of gradation values about regions predetermined by using the center locations of the reference image detected by the second center location detecting portion as a criterion; and a summation comparing portion for calculating differences between the summation of gradation values obtained by the first summation calculation portion and the summation of gradation values obtained by the second summation calculation portion, and detecting defects for the opening pattern based on the calculation result.

2. The pattern inspection device according to claim 1, wherein the first and second center location detecting portions detect the locations of edges of four sides of the opening patterns, and detect the centers of the opening patterns by using the center of each pair of the detected edges in the X direction and Y direction.

3. The pattern inspection device according to claim 1, wherein the second summation calculation portion calculates:

the summation of gradation values about regions predetermined so as to have a size almost the same as the opening size of the opening pattern;

decides whether the summation of gradation values is not less than the predetermined criterion or not; and identifies the opening pattern as a contact pattern if the summation of gradation values is not less than the predetermined criterion.

4. The pattern inspection device according to claim 3, wherein the summation comparing portion detects the defect of the opening pattern if the second summation calculation portion identifies the opening pattern as a contact pattern.

5. The pattern inspection device according to claim 3, wherein the first and second summation calculation portions calculate the summation of gradation values about regions having a size smaller than the opening size of the opening pattern.

6. A method of inspecting a pattern, comprising:

obtaining a picked-up image by picking up an image of a pattern formation member in which a plurality of opening patterns are formed;

obtaining a reference image used for comparing with the picked-up image;

detecting center locations of a plurality of opening pattern images included in the picked-up image;

detecting center locations of a plurality of opening pattern images included in the reference image;

calculating a summation of gradation values about regions predetermined by using the detected center locations of the picked-up image as a criterion;

calculating a summation of gradation values about regions predetermined by using the detected center locations of the reference image as a criterion; and calculating differences between the summation of gradation values calculated from pick-up image and the summation of gradation values calculated from reference image, and detecting a defect for each of the opening pattern based on the calculation result.

7. The method of inspecting a pattern according to claim 6, comprising;

detecting locations of edges of four sides of the opening patterns on the image and the reference image, and detecting centers of the opening patterns on the pick-up image and reference image by using the centers of pairs of the detected edges in the X direction and the Y direction.

8. The method of inspecting a pattern according to claim 6, comprising;

calculating a summation of gradation values about regions predetermined from the reference image so as to have a size almost the same as an opening size of the opening pattern, deciding whether the summation of gradation values is less than the predetermined criterion or not, and identifying the opening pattern as a contact pattern if the summation of gradation values is not less than the predetermined criterion.

9. The method of inspecting a pattern according to claim 8, comprising detecting the defect of the opening pattern if identified the opening pattern as a contact pattern.

10. The method of inspecting a pattern according to claim 8, comprising calculating the summation of gradation values about regions having a size smaller than each of the opening size of the opening patterns of the pick-up image and the reference image.

11. The method of inspecting a pattern according to claim 6, wherein:

the pattern formation member is a photomask used for manufacturing a semiconductor device; and the opening pattern is a contact pattern used for forming contact holes in the contact layer of the semiconductor device.

* * * * *